United States Patent [19]
Delmore et al.

[11] Patent Number: 5,939,339
[45] Date of Patent: *Aug. 17, 1999

[54] ABSORBENT SELF ADHERING ELASTIC BANDAGE

[75] Inventors: Michael D. Delmore, Mounds View; Scott A. Burton, Woodbury; Nicholas R. Baumann, St. Paul, all of Minn.

[73] Assignee: 3M Innovative Properties Company, St. Paul, Minn.

[ * ] Notice: This patent issued on a continued prosecution application filed under 37 CFR 1.53(d), and is subject to the twenty year patent term provisions of 35 U.S.C. 154(a)(2).

[21] Appl. No.: 08/726,873

[22] Filed: Oct. 4, 1996

Related U.S. Application Data

[63] Continuation of application No. 08/493,294, Jun. 21, 1995, abandoned, which is a continuation of application No. 08/288,453, Aug. 9, 1994, abandoned, which is a continuation-in-part of application No. 07/918,411, Jul. 22, 1992, abandoned.

[51] Int. Cl.$^6$ ............................... B32B 7/12; B32B 7/14
[52] U.S. Cl. ..................... 442/149; 428/354; 442/151; 602/44; 602/45; 602/46; 602/58; 602/76; 602/77
[58] Field of Search .................... 428/354, 41.7, 428/41.8; 602/44, 45, 46, 58, 76, 77; 442/149, 151

[56] References Cited

U.S. PATENT DOCUMENTS

| | | | |
|---|---|---|---|
| 2,093,910 | 9/1937 | Farrell | 602/77 |
| 2,190,378 | 7/1940 | Hinkamp et al. | 128/156 |
| 3,120,229 | 2/1964 | Hinkamp | 602/77 |
| 3,575,782 | 4/1971 | Hansen | 161/141 |
| 3,692,618 | 9/1972 | Dorschner et al. | 161/72 |
| 3,842,832 | 10/1974 | Wideman et al. | 128/169 |
| 3,908,645 | 9/1975 | Sandvig | 128/97 |
| 4,005,709 | 2/1977 | Laerdal | 128/155 |
| 4,209,563 | 6/1980 | Sisson | 428/288 |
| 4,349,020 | 9/1982 | Krikorian | 128/155 |
| 4,414,970 | 11/1983 | Berry | 128/156 |
| 4,552,802 | 11/1985 | Mechin | 428/255 |
| 4,609,578 | 9/1986 | Reed | 428/76 |
| 4,640,859 | 2/1987 | Hansen et al. | 428/105 |
| 4,659,609 | 4/1987 | Lamers et al. | 428/194 |
| 4,660,228 | 4/1987 | Ogawa et al. | 2/167 |
| 4,692,368 | 9/1987 | Taylor et al. | 428/137 |
| 4,692,371 | 9/1987 | Morman et al. | 428/224 |

(List continued on next page.)

FOREIGN PATENT DOCUMENTS

| | | | |
|---|---|---|---|
| 0 097 517 | 1/1984 | European Pat. Off. | A61F 13/00 |
| 0 212 284 | 3/1987 | European Pat. Off. | D04H 13/00 |
| 2 116 810 | 7/1972 | France | A61F 13/00 |
| 2116810 | 7/1972 | France | 602/76 |
| 25 15 786 | 10/1975 | Germany | A61F 13/00 |
| 54-076632 | 6/1979 | Japan . | |
| 1 575 830 | 1/1980 | United Kingdom | B32B 5/26 |

OTHER PUBLICATIONS

S. Thomas, "Bandages and Bandaging: The Science Behind the Art", *Care Science and Practice*, vol. 8, No.2, pp. 56–59 (1990).

*Primary Examiner*—Jenna Davis
*Attorney, Agent, or Firm*—Stephen W. Bauer; Paul W. Busse; Amelia A. Buharin

[57] ABSTRACT

The present invention relates to a wound dressing 10 that is a porous, self-adhering elastic 14 bandage which may be compressively wrapped around a wound and which is capable of absorbing fluids and wound exudate. A preferred embodiment of the wound dressing 10 is a self-adhering elastic substrate 14 which does not adhere to clothing, hair or skin having a compressive force when extended that provides a therapeutic benefit and which is flexibly attached or fixed to an absorbent layer 12.

20 Claims, 1 Drawing Sheet

U.S. PATENT DOCUMENTS

| | | | |
|---|---|---|---|
| 4,699,133 | 10/1987 | Schafer et al. | 128/156 |
| 4,707,398 | 11/1987 | Boggs | 428/224 |
| 4,724,184 | 2/1988 | Killian et al. | 428/227 |
| 4,741,949 | 5/1988 | Morman et al. | 428/224 |
| 4,773,903 | 9/1988 | Weisman et al. | 604/368 |
| 4,789,699 | 12/1988 | Kieffer et al. | 524/271 |
| 4,813,948 | 3/1989 | Insley | 604/366 |
| 4,957,795 | 9/1990 | Riedle | 428/74 |
| 4,984,584 | 1/1991 | Hansen et al. | 128/898 |
| 4,988,560 | 1/1991 | Meyer et al. | 428/297 |
| 5,027,803 | 7/1991 | Scholz et al. | 128/89 R |
| 5,061,258 | 10/1991 | Martz | 604/307 |
| 5,230,701 | 7/1993 | Meyer et al. | 602/76 |

ABSORBENT SELF ADHERING ELASTIC BANDAGE

This application is a continuation of U.S. Ser. No. 08/493,294 filed Jun. 21, 1995, abandoned, which is a continuation of U.S. Ser. No. 08/288,453 filed Aug. 9, 1994, abandoned, which is a continuation-in-part of U.S. Ser. No. 07/918,411 filed Jul. 22, 1992, abandoned.

The present invention relates generally to a wound dressing and, more particularly, to a wound dressing that is a multi-layer, self-adhering elastomeric bandage which may be compressively wrapped around a wound and is capable of absorbing fluids and wound exudate.

BACKGROUND

A wide variety of materials have been used to treat or dress different types or kinds of wounds. Typical materials that are used in the various dressings include wound contact materials and absorbent materials as well as compressive materials which are used to hold the wound contact and absorbent materials in place and which provide compressive force to the wound. For example, chronic wounds such as venous stasis ulcers have commonly been treated or dressed by wrapping as many as four separate layers each of a different type of material around the leg. Specifically, a four layer bandage developed at Charing Cross Hospital, London, includes an inner exudate absorbent layer (VELBRAND wrap, Johnson & Johnson, New Brunswick, N.J.), a crepe bandage, a compressive bandage (ELSET bandage, Seton) and an elastomeric wrap (COBAN self-adherent elastomeric bandage, 3M, St. Paul, Minn.). The use of multiple layers of different materials adds considerable time and expense both to the dressing itself and to the process of applying and changing the dressing.

Elastic fabric wraps are often used as an outer layer of compression wound dressings in order to hold the inner layers in place and to apply compression to the wound. The use of fabric elastomeric wraps, however, is not always desirable because dressings wrapped with elastic fabrics are likely to slip or shift after being applied which may result in insufficient compression being applied to the wound by the dressing or which may cause discomfort to the patient. Attempts to overcome the problems of slipping or shifting include applying a hydrocolloid adhesive to one side of the fabric wrap. The hydrocolloid adhesive is intended to stick to skin in order to prevent slippage (a bandage of this type is commercially available and is sold as DUODERM adhesive compression bandage, ConvaTec, Princeton, N.J.). Furthermore, many elastic fabrics do not have the capability of absorbing fluids.

In addition to the elastic fabric bandages referred to above, a variety of other wound dressings or bandage materials have been reported. A elastomeric self-adhering bandage is reported in U.S. Pat. Nos. 3,575,782 to Hansen and 4,984,584 to Hansen et al. According to the disclosure of these patents, elastic yarns are bonded between two layers of a nonwoven web with latex rubber to provide a bandage having good compression characteristics and cohesiveness or the ability to self adhere. The reported elastic bandage, however, does not have the capability of absorbing fluids and therefore could not be used alone as a satisfactory wound dressing. Another elastic self-adhesive, cohesive bandage is reported in U.S. Pat. No. 4,699,133 to Schafer et al. The Schafer et al. bandage is reported to provide permanent elastic compression by use of elastic threads in a woven fabric which is coated with self-adhering particles. The Schafer et al. bandage also does not have the capability of absorbing fluids.

Another type of elastic material is reported in U.S. Pat. No. 4,707,398 to Boggs that discloses an elastomeric nonwoven web that is formed from meltblown fibers. The nonwoven web is reported to be an absorbent material but is not reported to be self-adhering. Other nonwoven elastic web materials are reported in U.S. Pat. Nos. 4,663,220 to Wisneski et al., 4,720,415 to Vander Wielen et al., 4,789,699 to Kieffer, and 5,230,701 to Meyer et al. An absorbent nonwoven material is reported in U.S. Pat. No. 4,957,795 to Riedel. The Riedel material is reported to be a web of elastomeric melt-blown fibers and absorbent fibers dispersed in a nonwoven matrix. A wound dressing having a fluid permeable wound contact layer, the melt-blown absorbent layer and a soft compliant cover layer is also disclosed.

Yet another type of wound dressing material is reported in U.K. Patent 1 575 830 that discloses an absorbent dressing having an absorbent layer laminated to a plastic backing film. The backing film is reported to be a flexible, easily stretchable film but is not self-adhering.

A need exists for a unitary wound dressing which retains exudate and is self-adhering, absorbent, flexible and conformable, as well as capable of maintaining a therapeutic compressive force at the wound site for extended periods of time. In addition, a desired wound dressing should have the capability of being easy to apply and remove as well as being easily repositioned or rewrapped without losing any of the other desirable properties listed above.

SUMMARY OF THE INVENTION

The present invention provides an absorbent, self-adhering elastic wound dressing as well as a method of applying a compressive dressing to a wound. The elastic wound dressing of the present invention includes a porous, self-adhering elastic substrate which does not adhere to clothing, hair or skin and which has a permanent compressive force when extended that is sufficient to hold the dressing in place and to provide a therapeutic effect to the wound, an absorbent layer covering at least a portion of the self-adhering substrate, and means adapted to flexibly bond the self-adhering substrate to the absorbent layer.

A preferred embodiment of the present invention includes an elastic wound dressing having a porous, self-adhering elastic substrate made of partially extended, longitudinally aligned spandex yarns bound with a natural rubber latex between two porous, nonwoven polyester webs to give an elastic web that does not adhere to clothing, hair or skin, an absorbent layer that is bonded to at least one side of the elastic substrate with a biocompatible adhesive adapted to flexibly bond the substrate to the absorbent layer such that the adhesive is substantially contained on or within the substrate without filling the pores of the substrate.

A preferred absorbent layer is a foam, woven or nonwoven material including but not limited to rayon, polyester, polyurethane, polyolefin, cellulose, cellulose derivatives, cotton, orlon, nylon, or hydrogel polymeric materials. See, e.g., U.S. Pat. No. 4,773,903 to Weisman et al. An alternative absorbent layer includes a composite material comprising a nonwoven polymeric matrix and a highly hydrophilic fluid absorbing material. A particularly preferred composite material is a nonwoven matrix combined with a highly hydrophilic fluid absorbing material such as a polymeric absorbent fiber or particle selected from the group consisting of modified starches and high molecular weight acrylic polymers containing hydrophilic groups such as acrylonitrile fibers treated with alkali metal hydroxides. Suitable absorbent materials will preferably absorb at least about 25% by weight of fluid or exudate, and more preferably greater than about 100% by weight, when measured using test methods reported in U.S. Pat. No. 4,957,795 to Riedel.

A variety of means are suitable for attaching or fixing the elastic substrate to the absorbent layer such as stitching, needle-tacking, ultrasonic welding or bonding with a suitable adhesive. A preferred adhesive is a biocompatible adhesive that is selected from the group consisting of natural rubber based adhesives and acrylic based adhesives.

The present invention also includes a method of applying a compressive dressing to a wound which includes the step of wrapping the wound with a compressive bandage that is preferably a self-adhering elastic substrate which does not adhere to clothing, hair or skin and which has a permanent compressive force when extended sufficient to hold the dressing in place and to provide a therapeutic effect to the wound, an absorbent layer covering at least a portion of the self-adhering substrate, and means adapted to flexibly bond the self-adhering substrate to the absorbent layer.

The present method is particularly adapted for treating or dressing an injured finger, toe, hand, foot, limb, torso, or head by wrapping the elastic bandage of the present invention around the body part at the site of the injury.

DETAILED DESCRIPTION

Figure 1:
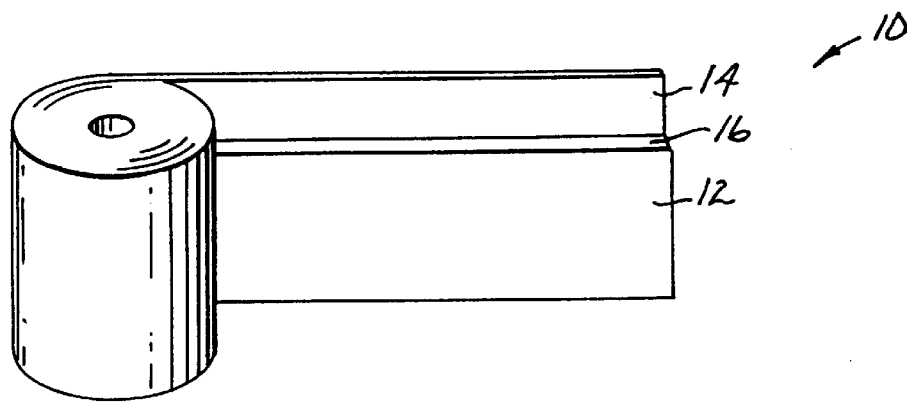
FIG. 1 is a perspective view of a wound dressing having an elastic substrate and an absorbent layer.

An absorbent, self-adherent, elastic dressing of the present invention includes a porous, self-adherent elastic substrate which is attached or fixed to an absorbent layer. In one embodiment of the invention, the absorbent layer covers all or a substantial portion of a self-adherent elastic substrate. As illustrated in FIG. 1, a roll of a wound dressing of the invention 10 includes an absorbent layer 12 which covers a substantial portion of an elastic substrate 14. The portion of the elastic substrate which is not covered by the absorbent layer 16 is adapted to directly contact the side of the elastic substrate opposite of the absorbent layer or the back of the elastic substrate when the dressing is wrapped around a body part such as a leg. This contact allows the dressing to adhere to itself and prevents sliding or shifting of the wrap after it is in place. At the end of the bandage, the absorbent layer does not cover the elastic substrate in order to provide a large contact area at the end of the wrapped portion of the bandage. In some applications, the absorbent layer may be removed from the elastic substrate in order for the last wrap of the bandage to allow about one wrap of elastic substrate onto itself. In a preferred dressing a tab of nonadherent material is added to the very end of the wrap in order to allow the wrap to be easily unwound for dressing repositioning or changing.

The self-adherent, elastic substrate is adapted to provide compressive force to the wound and is typically made of materials having high elastic recovery and a corresponding low elastic hysteresis. Suitable elastic substrates have a stretch of at least 100% with a recovery of about 90%. A suitable method to measure stretch is reported in U.S. Pat. No. 4,984,584 to Hansen et al. The compressive recovery of the material is retained throughout the time period the dressing is in place.

In use, a preferred substrate will provide a compressive force of between about 1–60 mm Hg when wrapped around a wound. This pressure is generally sufficient to provide a therapeutic benefit without impeding or restricting arterial blood flow. A suitable method to measure compressive force for a wrap is reported in Thomas, *Care Science and Practice*, 8:56–60 (1990). Therapeutic benefits provided by the present invention include reduction of swelling, edema and clot promotion and improved circulation.

Materials suitable for use as an elastic substrate in the present invention include materials which are elastic, conformable, porous, provide adequate compression and which are self-adhering. In general, the material is sufficiently porous if the material allows for the transmission of air and moisture vapor through the material. In addition, materials which may be sterilized, including radiation sterilized, are preferred. Commercially available examples of elastic substrates suitable for use in the present invention include woven bandages such as CUTTER-WRAP self-adhesive bandage (Cutter Animal Health, Miles Laboratories, Inc., Shawnee, Kans.), MEDI-RIP self-adherent bandage (Conco Medical Company, Bridgeport, Conn.) or SELF-GRIP sports tape/bandage (LMA, Ltd., South Norwalk, Conn.) and nonwoven bandages such as ROFLEX cohesive flexible bandage (Smith and Nephew Rolyan Inc., Menomonee Falls, Wis.), VET-FLEX veterinary flexible bandage (The Butler Company, Columbus, Ohio), CO-FLEX cohesive flexible bandage (Andover Coated Products, Inc., Marblehead, Mass.), FLEXUS support wrap (Kimberly-Clark Corporation Animal Care Division, Roswell, Ga.), COBAN self-adherent wrap (3M, St. Paul, Minn.), or EQUISPORT equine support bandage (3M, St. Paul, Minn.).

Preferred materials for use as the elastic substrate in the present invention are COBAN self-adherent elastomeric bandage and EQUISPORT equine support bandage. COBAN is a self-adherent material which does not stick to skin or hair and which does not traumatize skin during the bandage wear period. EQUISPORT equine support bandage is a self-adherent material related to COBAN elastomeric bandage except that it is able to provide a greater amount of compression when used. Methods suitable to make these self adherent materials are reported in U.S. Pat. Nos. 3,575,782 to Hansen and 4,984,584 to Hansen et al. The increased compression is a result of using greater numbers of larger elastic strands in the material. For example, a material having elastic strands of about 550–1700 denier and about 15–25 strands per inch is suitable.

A material made of melt blown microfiber webs may also be used as the elastic substrate in the present invention. The melt blown microfiber webs may be composed of a variety of well known thermoplastic elastomers including polyurethane, polybutylene, styrene-isoprene block copolymer, styrene-butadiene block copolymer, (KRATON polymer, Shell Oil Company, Belpre, Ohio) and blends of these elastomers with polyolefins such as polypropylene and polyethylene. In addition, the melt blown microfiber webs may include, but are not limited to, staple fibers, such as rayon, polyester, nylon, cotton, LANSEAL fiber, cellulose, or polypropylene fibers, to provide a blend of elastomeric and staple fibers.

Melt blown microfiber webs for use in the present invention may be made using methods known in the art. The melt blown microfiber web is typically made by an extrusion process. Briefly, a polymeric material is melted and pumped by an extruder and forced through a die consisting of many small diameter holes and a compressed gas is injected onto either side of the die through a series of vents or ducts. The compressed gas draws and stretches the melt as it leaves the die. In addition the compressed gas rapidly cools, entangles, and transports the newly created fibers to a collection drum or belt. Representative methods are described in U.S. Pat. Nos. 4,813,948 to Insley, 4,988,560 to Meyer et al., 4,957,795 to Riedel, or 5,230,701 to Meyer et al. Suitable melt blown microfiber webs will have elongations of from about 30–500% with an elastic recovery of about 90% and will have a peak load of at least about several pounds per inch when measured using well known procedures. See, e.g., the test procedures reported in U.S. Pat. No. 4,984,584 to Hansen et al.

The self-adhering properties of melt blown microfiber webs may be enhanced by coating these materials with natural rubber latex or adhesives having low tack. The latex or low tack adhesive is preferably coated onto both sides of the elastic substrate in the amount of about 0.01–75 wt. % in order to provide for self-adherence or self-bonding when the substrate is wrapped around a wound.

Another suitable material for use as the elastic substrate in this invention is a spunbond material. Spunbonding typically entails extruding a multiplicity of continuous thermoplastic strands through a multiplicity of die orifices onto a moving surface on which the extruded polymeric strands are collected in a randomly distributed fashion. The randomly distributed polymeric strands are then bonded together in a manner to provide sufficient integrity to the resulting nonwoven web. Spunbond materials generally exhibit a high strength to weight ratio as well as high porosity. A general description of the methods used to make spunbond materials is reported in U.S. Pat. No. 3,692,618 to Dorschner et al.

In the embodiment illustrated by FIG. 1, the absorbent material both absorbs wound exudate and protects the wound by absorbing shock. A variety of materials may be used as the absorbent layer in this invention including foams, woven or nonwoven materials such as rayon, polyester, polyurethane, polyolefin, cellulose, cellulose derivatives, cotton, orlon, nylon, and hydrogel polymeric materials. Other types of materials having similar absorbent properties and characteristics would also be suitable for use in this invention. A preferred absorbent layer is a woven or nonwoven material of natural or synthetic fibers made from, but not limited to, rayon, polyester, polyurethane, polyolefin, cellulose, cellulose derivatives, cotton, orlon, nylon, or hydrogel polymeric materials. Examples of absorbent materials are dacron-polyester cast padding MW04, (3M, St. Paul, Minn.), DELTA-ROL acrylic cast padding 6884, (Johnson & Johnson, New Brunswick, N.J.), SOF-ROL 100% needle-tacked rayon cast padding HRI 8137-009034, (Johnson & Johnson, New Brunswick, N.J.), SPECIALIST cotton cast padding HRI 8137-009044 (Johnson & Johnson, New Brunswick, N.J.), WEBRIL cotton undercast padding 3175 (The Kendall Company, Boston, Mass.), WEBRIL II cotton undercast padding 4221 (The Kendall Company, Boston, Mass.), nonwoven cotton web 142–451 and nonwoven rayon/polyester web 140–037 (VeraTec Company, Wapole, Mass.), and an absorbent resilient open-cell foam such as polyurethane, polyester, polyether, polyolefin foams as described in U.S. Pat. No. 3,908,645 to Sandvig.

Other suitable absorbent materials include composite materials such as nonwoven polymeric matrices combined with highly hydrophilic fluid absorbing materials. Highly hydrophilic fluid absorbing materials include polymeric absorbent fibers or particles selected from the group consisting of modified polysaccharides, modified polyurethanes, and high molecular weight acrylic polymers containing hydrophilic groups. A preferred highly hydrophilic fluid absorbing material is acrylonitrile fibers treated with alkali metal hydroxides. A commercially available hydrogel polymeric material is available under the tradename LANSEAL fiber (Japan Exlan Co., Ltd., Osaka, Japan). These types of composite absorbent materials are readily prepared using well known methods such as the method reported in U.S. Pat. No. 4,957,795 to Riedel.

Typically, the absorbent material includes one or more layers of a nonwoven, melt blown absorbent fiber which provides loft to the material and which absorbs liquids. The surface of the absorbent material which contacts the wound may additionally be treated or modified so that it will not adhere to the wound. For example, the absorbent material may be covered with a variety of commercially available wound contact materials such as TEGAPORE woven nylon web, TEGADERM polyurethane film or TEGASORB hydrocolloid (all available from 3M, St. Paul, Minn.) as well as other well known related materials. Preferably, absorbent material is selected so that when it is attached or fixed to the elastic substrate it will not inhibit the expansion or contraction of the elastic substrate. For example, if an absorbent material is compressible the absorbent material may be attached or fixed to the elastic substrate when the substrate is stretched or extended and then when the elastic substrate is relaxed the absorbent layer is compressed without bunching or becoming too stiff.

Figure 2:
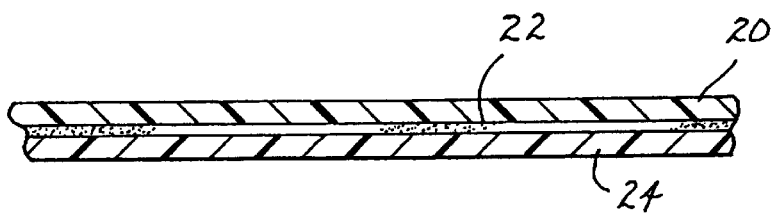
FIG. 2 is a side view of a wound dressing having an elastic substrate and an absorbent layer.

FIG. 2 illustrates the materials which are used to make a dressing of the present invention having two layers which are adhesively bonded together. The elastomeric material 24 is preferably stretched and a suitable adhesive 22 is applied to the stretched material. After the adhesive is applied, the absorbent layer 20 is bonded to the stretched elastomeric substrate to give a laminated article. After the adhesive has cured or dried, the elastomeric laminated article is allowed to relax to an unstretched state. Suitable adhesives which may be used to bind an absorbent layer to an elastic substrate of the present invention include pressure sensitive adhesives such as polyacrylates, polyvinylethers, and poly alpha-olefins, as well as polymers which may be formulated with appropriate tackifiers such as natural rubber, styrene-isoprene block copolymer, silicone rubber, cis-polyisoprene, styrene butadiene, and cis-polybutadiene, hot-melt adhesives such as low-density polyethylene, ethylene-vinyl acetate copolymers, ethylene-ethyl acrylate copolymers, paraffin waxes, polyesters, polyamides, polypropylene, styrene-butadiene block copolymers and polyurethanes, and curable adhesives such as silicones and urethanes. In addition, repositionable adhesives such as microsphere pressure sensitive adhesives may be used to bond the absorbent layer to the elastic substrate. Highly preferred adhesives would be those which are biocompatible with skin and which generally do not cause irritation or undesirable sensitivity reactions when in contact with skin for extended periods of time under normal conditions such as natural rubber and acrylate based adhesives.

A wide variety of materials are available to bandage or dress a small cut or abrasion to a finger, toe, hand, foot, or limb. The most common are adhesive coated bandages such as BAND-AID adhesive bandages (Johnson & Johnson, New Brunswick, N.J.). Adhesive bandages usually consist of an elastic backing of perforated plastic or of a woven or knit fabric. The backing is covered on one side with a pressure sensitive adhesive. A gauze or absorbent pad is placed in the center of and adhered to the adhesive side of the backing material.

Simple wounds such as minor cuts, scrapes, and abrasions on fingers, hands, arms, feet or legs may be routinely treated or dressed with well known commercially available adhesive bandages. Even for these common uses, adhesive based bandages suffer from some well known deficiencies. For example, adhesive bandages are typically not repositionable, once adhered to the skin an adhesive bandage either stays as put or it must be discarded. Further, most adhesive bandages fall off when wet. In addition, adhesive bandages generally do not adhere well to joint areas or areas of high flexibility such as elbows or knees. Removal of adhesive bandages can also be problematic if the adhesive bandage is adhered to skin and body hair and adhesive residue is often left on the skin. The adhesives used also limit vapor transmission, which can cause localized skin maceration.

Small, absorbent, self adherent elastic dressings of the present invention may be used in place of BAND-AID bandages and other related products to cover cuts, scrapes, and abrasions of fingers or toes. Similar but larger elastic dressings may be used to cover wounds of hands, arms, feet, legs, torso, or head.

Figure 3:
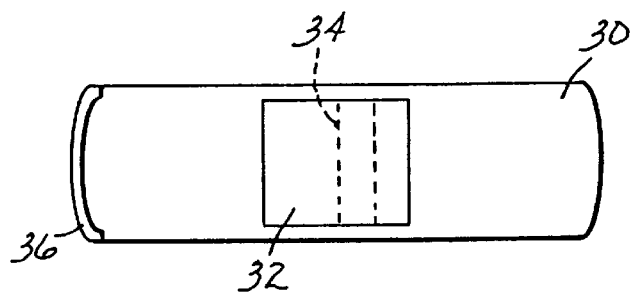
FIG. 3 is a plan view of a wound dressing suitable to dress cuts and scrapes of fingers and toes.

As illustrated in FIG. 3, an embodiment of the present invention suitable for dressing fingers or toes includes an elastomeric substrate 30 and an absorbent pad 32 which is bonded to the elastic substrate with a layer of adhesive 34 which is shown in phantom in FIG. 3. The adhesive strip may be applied as a thin strip when the absorbent pad is relatively stiff or inflexible in order to minimally inhibit the expansion or contraction of the elastic substrate. A thin strip of adhesive on such an absorbent pad allows the elastic substrate to expand and contract by sliding past the pad. In addition, a small portion of the elastic substrate 34 is coated with a small amount of material to form tab 36 that covers the self-adherent material on the elastic substrate so that the end of the elastic substrate may be readily located and lifted to allow facile removal or repositioning of the dressing. A suitable material to cover the self-adherent material is a food grade printing ink.

When used, the absorbent pad contacts and covers the wound of a finger or toe while the elastic substrate wraps around the finger or toe and then wraps back onto and adheres to itself. The absorbent pad is preferably offset to one end of the elastic substrate to provide greater ease of application.

Typical sizes of small elastic wraps suitable for treating fingers and toes are about ⅜–1 inch in width by 3–4 inches in length. These small wraps are readily packaged and sterilized using processes, such as gamma irradiation, that are well known in the art. Elastic wraps of the present invention of about 1–4 inches in width and by 12–24 inches in length are properly sized to treat or dress arms, elbows, legs, and knees.

Figure 4:
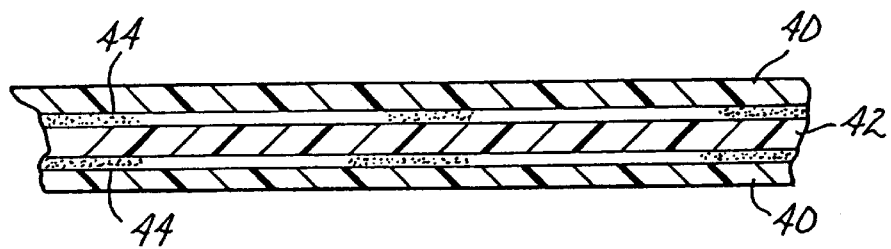
FIG. 4 is a side view of a wound dressing having an absorbent layer sandwiched between two elastic substrates.

An alternate embodiment of the present invention having more than two layers is illustrated in FIG. 4. FIG. 4 illustrates a wound dressing having three layers which are adhesively bonded together. Specifically, an absorbent layer 42 is sandwiched between two elastic layers 40. The elastic layers and the absorbent layer are bonded together by a suitable adhesive 44.

Those of ordinary skill in the art would readily recognize that wound dressings having more than three layers are also provided by the present invention.

The following examples are provided to further illustrate the practice of the present invention. The examples are not intended to limit the invention which is defined in the appended claims.

EXAMPLE 1

Leg Wrap

A wound dressing that is suitable for use as a leg wrap was prepared from a 2.0 m length of COBAN 1584 self-adherent wrap (3M, St. Paul, Minn.) that was unwound from a roll of the wrap and stretched to a length of 3.2 m (COBAN 1584 wrap is 100 mm wide and 4.5 m long wrapped on a one inch diameter core. The wrap has an elastic elongation of 100% with a recovery of greater than 90%). The stretched wrap was secured at both ends and an area along one edge was masked over the entire 3.2 m length of the material with tape (SCOTCH brand MAGIC MENDING tape, 3M, St. Paul, Minn.). The width of the masked area was 12 mm. In addition, 0.2 m of the end of the stretched wrap was also masked. The unmasked area of the wrap was then covered with a spray adhesive (3M Super 77 Spray Adhesive, 3M, St. Paul, Minn.) with an adhesive add-on of about 23 g/m$^2$. An absorbent web (1.5 inches long, 1.5 denier polyester staple fiber carded web 100 g/m$^2$, Hoescht Celanese, Portsmouth, Va.) 88 mm wide and 3.0 m long was also covered with a spray adhesive (3M Super 77 Spray Adhesive, 3M, St. Paul, Minn.) with an adhesive add-on of about 23 g/m$^2$ and then the adhesive treated sides of the elastic and absorbent materials were mated together taking care to align the absorbent web adjacent to the masked portion of the elastic material. Pressure was then applied to the two materials using a roller. The tape on the masked portion was then removed and the elastic material was allowed to relax. The bonded dressing was then rewound onto a one inch diameter core.

EXAMPLE 2

Multi-layer Wrap

A multi-layer wrap was prepared using the process described in Example 1, above, by applying the spray adhesive to the exposed surface of the absorbent layer and then bonding a second 3.2 m stretched length of COBAN 1584 wrap onto the absorbent layer. The laminated dressing was rolled to ensure bonding, the tape was removed and the stretched substrate was allowed to relax.

EXAMPLE 3

Small Wrap

A small elastic bandage suitable to treat a wound of the finger was prepared from the following components:
  a) COBAN self-adherent wrap (3M, St. Paul, Minn.) having ten 280 denier spandex elastic yarns per inch width (Globe Manufacturing Co., Fall River, Mass.) bonded between two polyethylene terephthalate cover webs (0.25–0.5 oz/yd$^2$, 1.5 denier fibers bonded together with 25 wt. % of a polyethylacrylate resin, 3M, Hutchinson, Minn.) with a concentrated solution of natural rubber latex (GNL 200, Goodyear Tire and Rubber Co., Akron, Ohio),
  b) an absorbent pad made of a nonwoven web of rayon fibers (1.5 denier fibers, mean basis weight 100 g/m$^2$, Courtaulds Fiber Inc., Lemoyne, Ala.) coated on both sides of the web with a discontinuous, porous, non-stick layer of low density polyethylene (0.0008 inch thick, Consolidated Thermoplastics Co., Chippewa Falls, Wis.) which was applied to the web under heat and pressure, and c) a three-eighths inch wide transfer adhesive (Scotch Brand 465 transfer adhesive, 3M, St. Paul, Minn.).

To prepare the small elastic bandage, the COBAN wrap was cut into strips (19 mm×76 mm) having the elastic fibers lengthwise and the end of the strips were rounded to a 13 mm radius. A rectangular absorbent pad (13 mm×25 mm) was adhered to the COBAN strip with a length of the transfer adhesive (13 mm). The rectangular pad was centrally positioned on the COBAN strip about 13 mm from one end. The assembled wrap was placed in a heat sealable paper/polyethylene package (Thilmany Pulp and Paper Co, KanKauna, Wis.) and sealed. The packaged wraps were then sterilized with gamma radiation at 2.5 megarads.

EXAMPLE 4

Melt Blown Microfiber Wrap

A 4"×4" unstretched elastic web of a KRATON melt blown elastomer sandwiched between two layers of a spunbond polypropylene (taken from a side panel of a HUGGIES brand PULL-UPS disposable Training Pants (Kimberly-Clark Corp., Neenah, Wis.) was spray coated with a solution of natural latex rubber (1:1 dilution with water; GNL 200, Goodyear Tire and Rubber Co., Akron, Ohio) and allowed to air dry such that approximately 0.5 g dry latex was applied to each side of the unstretched web. The sprayed web was cut into a 1"×2" strip where the elasticity is in the waft direction.

A 4"×4" piece of dacron/polyester cast padding, (MSO4, 3M, St. Paul, Minn.) was similarly spray coated with the above natural latex rubber solution and allowed to air dry. A ¾" by ¾" piece of absorbent was cut from the coated padding and placed in the center of the above 1"×2" self-adherent web. The two layers were bonded together by application of moderate pressure to form an elastic wound dressing.

EXAMPLE 5

Nonwoven Elastomeric Wrap

A nonwoven web comprised of 100% 1.5 denier rayon staple fiber (Courtalds, Suffolk, Va.) was formed using a Rando-Webber model number 12 BS (Curlator Corp., East Rochester, N.Y.) to give a nonwoven web twelve inches wide and twenty feet long. The basis weight of this nonwoven web was 100 g/m². The nonwoven web was then cut to a width of six inches and a length of one foot and needletacked by a needletacker (James Hunter Machine Co., North Adams, Mass.) at a line speed of 10 ft./min. with needles spaced 3 per inch. After needletacking the basis weight was approximately 110 g/m².

This needletacked rayon nonwoven web was then flexibly secured to a six inch wide and one foot long COBAN elastic substrate by needletacking the rayon web into the COBAN using the same needletacker as above while the COBAN was held in its elongated state. After needletacking at a line speed of 10 ft./min. the laminate of rayon and COBAN was allowed to relax, giving an elastic, absorbent bandage.

EXAMPLE 6

Nonwoven Elastomeric Wrap

A nonwoven web suitable for the absorbent layer was prepared as in Example 5 using the following blend of fibers, 35% MELTY fiber (Hoescht Celanese, Portsmouth, Va.), 30% LANSEAL absorbent fiber (Japan Exlan Co., LTD., Osaka, Japan), 25% T294 6 denier polyester staple fiber (Hoescht Celanese), and 10% T121 1.2 denier polyester staple fiber (Hoescht Celanese).

The MELTY fiber is a sheath/core fiber that incorporates a strong core of polyester coated with a sheath of a polyethylene having a lower melting point than the core, and thus is able to thermally bond at lower temperatures.

This nonwoven web of blended fibers was then needletacked as in Example 5, cut to a width of 88 mm and a length of 3.2 m and adhesively attached to the COBAN substrate as in Example 1.

EXAMPLE 7

Nonwoven Elastomeric Wrap

A nonwoven web suitable for the absorbent layer was prepared as in Example 5 using the following blend of fibers, 50% 1.5 denier rayon staple fiber (Courtalds, Suffolk, Va.) and 50% LANSEAL absorbent fiber (Japan Exlan Co., LTD, Osaka, Japan).

This nonwoven web of blended fibers was then cut to a width of 88 mm and a length of 3.2 mm and needletacked as in Example 5 and either adhesively attached to a COBAN substrate as in Example 1 or needletacked to a COBAN substrate as in Example 5.

EXAMPLE 8

Nonwoven Elastomeric Wrap

A nonwoven web was prepared of blended fiber as in Example 5 and needletacked to a GELOK super absorbent paper (Gelok Corp., Dunbridge, Ohio). GELOK paper is a three layer laminate of tissue paper on either side of a crosslinked starch super absorbent polymer particle.

This laminate of a blended fiber nonwoven web and GELOK super absorbent paper was then cut to a width of 88 mm and a length of 3.2 m and adhesively laminated to the COBAN substrate as in Example 1 with the GELOK paper next to the COBRAN substrate.

EXAMPLE 9

Nonwoven Elastomeric Wrap

A nonwoven web suitable for the absorbent layer was prepared as in Example 5 using 100% cotton staple fibers (Cotton Inc., New York, N.Y.) with a basis weight of 100 g/m² and cut to a width of 88 mm and a length of 3.2 m and needletacked as in Example 5. This nonwoven was then adhesively laminated to the COBAN substrate as in Example 1.

EXAMPLE 10

Venous Stasis Ulcer Dressing

A patient's lower leg and ulcer are cleaned and a primary wound contact dressing (TEGASORB, 3M, St. Paul, Minn.) is used to cover the ulcer. The lower leg is wrapped with the knee held in a slightly flexed position. The dressing is applied by wrapping the roll of absorbent self-adherent elastic dressing around the leg absorbent side facing the skin beginning at the base of the toes with a figure of eight turn around the ankle joint. Each wrap firmly overlaps earlier turns so that a graduated compressive pressure exists from at least 35–40 mm Hg at the ankle tapering down to approximately 17 mm Hg at the knee. The wrap is applied up to the tibial tuberosity of the knee and the end of the roll with self-adherent elastic material that is not covered with absorbent is wrapped around itself (the end of the roll is not covered with the absorbent layer). The uncovered strip that runs in the long direction of the roll will be in contact with and adhere to the underneath self-adherent elastomeric material so that the wrap does not slip during the wear period.

If only a partial roll is wrapped around the leg, the absorbent layer may be pulled away from the backing and trimmed to make an approximately one foot long self-adherent elastic "tail" that can be used to tack down the end of the roll.

EXAMPLE 11

Nonwoven Melt Blown Elastomeric Wrap

Elastomeric, nonwoven, melt blown, microfiber webs having basis weights of 20, 50, and 120 g/m$^2$ were prepared using thermoplastic, elastomeric polyurethane polymer (Morthane PS-440-200, a polyurethane available from Morton International, Inc., Chicago, Ill., with 4.0% tan pigment (color number 1093538 available from ReedSpectrum, a division of Sandoz Chemicals Corporation, Minneapolis, Minn.) and a process similar to the process reported in Wente, Van A., "Superfine Thermoplastic Fibers" in *Industrial Engineering Chemistry*, Vol. 48, pages 1342 et seq (1965), or in Report No. 4364 of the Naval Research Laboratories, published May 25, 1954 titled "Manufacture of Superfine Organic Fibers", by Wente, Van A., Boone, C. D. and Fluharty, E. L. except that the melt blowing die had smooth surface orifices (10 /cm) with an 8:1 length to diameter ratio. The die temperature was maintained at 226° C., the primary air temperature and pressure were 235° C. and 150 kPa, respectively (0.76 mm gap width), and the polymer throughput rate was 131 gm/hr/cm. The resulting webs had a fiber size of 5–10 microns, basis weights and thickness of 20 g/m$^2$ and 0.0076 mm, 50 g/m$^2$ and 0.105 mm, or 120 g/m$^2$ and 0.305 mm.

The melt blown nonwoven material prepared as described above (Morton 440-200 polyurethane, MBPU, consisting of three basis weights, 20, 50 and 120 g/m$^2$), were each cut at into two rectangular pieces approximately 6 by 8 inches.

Each rectangular piece was then coated with a hot pink pigmented natural latex rubber aqueous solution (Number 41-3701-0388-3, 3M, St. Paul, Minn.). The coating was accomplished by individually placing the cut pieces of MBPU into a aluminum tray and the latex solution was blotted on to each side of the sample using a polyester applicator that had been dripped into the latex. Then each coated sample was hung vertically in an oven at about 100° F. The samples were left in the oven overnight and were in the oven for approximately 16 to 20 hours.

The samples were removed and allowed to cool to room temperature. These dried samples were further processed into test specimens to be used for stress/strain analysis and actual samples of prototype finger bandages. The test specimens were die cut into hourglass shapes with a gauge width of 0.31 cm and a gauge length of 1.0 cm.

All the coated materials exhibited good to excellent cohesive properties. This observation was based on samples of the coated material which were cut into strips about 1 in.×3.5 in. (2.54 cm×8.9 cm) and wrapped around a finger over the second or first knuckle. The samples were then worn at least an hour through normal work routines that included frequent hand washings. In all cases the samples remained secured to the finger.

The 20 g/m$^2$ sample was very shear, self-adherent and provided an acceptable, low level of compression. The 50 g/m$^2$ sample was conformable and provided good but non-constricting level of compression. The 120 g/m$^2$ sample had good conformability and was capable of exerting a level of compression high enough to cause constriction of blood flow. In particular, when the wrap as applied to a digit it was observed that the tip of the digit wrapped with the 120 g/m$^2$ sample would become cold within minutes after the wrap was applied. The other two exemplified wraps, however, did not exert enough force to cause a digit tip to become cold even though these wraps were frequently removed and rewrapped with increasing levels of tension up to elongations of approximately 75%.

We claim:

1. A compressive dressing which may be used to treat a finger, hand, toe, foot, limb, torso or head wound or a surgical site comprising:
    a) a conformable, porous, self-adhering elastomeric substrate wherein the substrate does not adhere to clothing, hair or skin and which has a compressive force when extended that is sufficient to hold the dressing in place for a period of time to provide a therapeutic effect to the wound; and
    b) an absorbent layer flexibly bonded to the self-adhering substrate wherein the absorbent layer is offset to one end of the self adhering substrate.

2. A compressive dressing which may be used to treat a finger, hand, toe, foot, limb, torso or head wound or a surgical site comprising:
    a) a conformable, porous, self-adhering elastomeric substrate wherein the substrate does not adhere to clothing, hair or skin and which has a compressive force when extended that is sufficient to hold the dressing in place for a period of time to provide a therapeutic effect to the wound; and
    b) an absorbent layer flexibly bonded to the self-adhering substrate using a thin strip of adhesive positioned between the absorbent layer and the substrate allowing the elastic substrate to expand and contract by sliding past the pad.

3. A compressive dressing which may be used to treat a finger, hand, toe, foot, limb, torso or head wound or a surgical site comprising:
    a) a conformable, porous, self-adhering elastomeric substrate selected from the group consisting of partially extended, longitudinally aligned elastic yarns bound with a polymeric binder between two porous nonwoven fibrous webs and a conformable, porous, web of melt blown or spunbond, elastomeric polyurethane microfibers, wherein the substrate does not adhere to clothing, hair or skin and which has a permanent compressive force when extended which is sufficient to hold the dressing in place for a period of time to provide a therapeutic effect to the wound, and
    b) an absorbent layer covering at least a portion of the self-adhering substrate, wherein only a portion of the absorbent layer is bonded to the self-adhering substrate, whereby the absorbent layer minimally inhibits expansion or contraction of the self-adhering substrate.

4. A compressive dressing which may be used to treat a finger, hand, toe, foot, limb, torso or head wound or a surgical site comprising:

a) a conformable, porous, self-adhering elastomeric substrate selected from the group consisting of partially extended, longitudinally aligned elastic yarns bound with a polymeric binder between two porous nonwoven fibrous webs and a conformable, porous, web of melt blown or spunbond, elastomeric polyurethane microfibers, wherein the substrate does not adhere to clothing, hair or skin and which has a permanent compressive force when extended which is sufficient to hold the dressing in place for a period of time to provide a therapeutic effect to the wound, and b) a compressible absorbent layer flexibly bonded to and covering at least a portion of the self-adhering substrate, wherein the absorbent layer is compressed when the self-adhering substrate is in a relaxed state, and wherein the absorbent layer minimally inhibits the expansion or contraction of the self-adhering substrate.

5. A compressive dressing which may be used to treat a finger, hand, toe, foot, limb, torso or head wound or a surgical site comprising:

a) a conformable, porous, self-adhering elastomeric substrate selected from the group consisting of partially extended, longitudinally aligned elastic yarns bound with a polymeric binder between two porous nonwoven fibrous webs and a conformable, porous, web of melt blown or spunbond, elastomeric polyurethane microfibers, wherein the substrate does not adhere to clothing, hair or skin and which has a permanent compressive force when extended which is sufficient to hold the dressing in place for a period of time to provide a therapeutic effect to the wound, and b) an absorbent layer covering at least a portion of the self-adhering substrate wherein the absorbent layer comprises a stretchable foam.

6. A compressive dressing which may be used to treat a finger, hand, toe, foot, limb, torso or head wound or a surgical site comprising:

a) a conformable, porous, self-adhering substrate selected from the group consisting of partially extended, longitudinally aligned elastic yams bound with a polymeric binder between two porous nonwoven fibrous webs and a conformable, porous, web of melt blown or spunbond, elastomeric polyurethane microfibers, wherein the substrate does not adhere to clothing, hair or skin and which has a permanent compressive force when extended which is sufficient to hold the dressing in place for a period of time to provide a therapeutic effect to the wound, and b) an absorbent layer flexibly bonded to and covering at least a portion of the self-adhering substrate, wherein the self-adhering substrate is stretched before the absorbent layer is fixed by adhesive to the self-adhering substrate, wherein the absorbent layer minimally inhibits expansion or contraction of the self-adhering substrate.

7. The dressing of claim 3 wherein the self-adhering substrate comprises partially extended, longitudinally aligned spandex yarns bound between two porous nonwoven polyester webs with a natural rubber latex.

8. The dressing of claim 3 wherein the self-adhering substrate is a web of melt blown or spunbond elastomeric polyurethane microfibers having a polyurethane microfiber basis weight of about 20–120 $g/m^2$.

9. The dressing of claim 3 wherein the absorbent layer is a foam, woven or nonwoven material selected from the group consisting of rayon, polyester, polyurethane, polyolefin, cellulose, cellulose derivatives, cotton, orlon, and hydrogel polymeric material.

10. The dressing of claim 3 wherein the absorbent layer is a woven or nonwoven material of natural or synthetic fibers selected from the group consisting of rayon, polyester, polyurethane, polyolefin, cellulose, cellulose derivatives, cotton, orlon, nylon, and hydrogel polymeric material.

11. The dressing of claim 3 wherein the absorbent layer is a nonwoven polyester material.

12. The dressing of claim 3 wherein the absorbent layer is a nonwoven cellulose or cellulose derivative material.

13. The dressing of claim 12 wherein the nonwoven cellulose or cellulose derivative absorbent layer is coated with a discontinues polyolefin layer.

14. The dressing of claim 3 wherein the self-adhering substrate and absorbent layer are attached by a fastening method selected from the group consisting of stitching, ultrasonic welding, needletacking and bonding using a biocompatible adhesive.

15. The dressing of claim 14 wherein the biocompatible adhesive is selected from the group consisting of natural rubber based adhesives and acrylic based adhesives.

16. The dressing of claim 3 wherein a portion of the self-adhering substrate is not covered by the absorbent layer in order to allow the dressing to adhere to itself when the dressing is wrapped around a wound and to prevent sliding or shifting of the dressing after it is in place.

17. The dressing of claim 16 further comprising a tab of nonadherent material fixed to at least one end of the dressing which allows the dressing to be easily unwound for repositioning or changing.

18. The dressing of claim 3 suitable for dressing fingers or toes wherein the absorbent pad is bonded to the self-adhering substrate with a layer of adhesive.

19. The dressing of claim 18 wherein a small portion of the self-adhering substrate is coated with a small amount of material which covers a self-adherent material on the self-adhering substrate so that the end of the self-adhering substrate may be readily located and lifted to allow facile removal or repositioning of the dressing.

20. The dressing of claim 18 wherein the absorbent pad is offset to one end of the self-adhering substrate.

* * * * *

UNITED STATES PATENT AND TRADEMARK OFFICE
CERTIFICATE OF CORRECTION

PATENT NO.: 5,939,339

DATED: August 17, 1999

INVENTOR(S): Michael D. Delmore, Scott A. Burton and Nicholas R. Baumann

It is certified that error appears in the above-identified patent and that said Letters Patent is hereby corrected as shown below:

Col. 13, line 40, "yams" should read --yarns--.

Signed and Sealed this

Twenty-third Day of May, 2000

Attest:

Q. TODD DICKINSON

Attesting Officer      *Director of Patents and Trademarks*

UNITED STATES PATENT AND TRADEMARK OFFICE
CERTIFICATE OF CORRECTION

PATENT NO.   : 5,939,339  
DATED        : August 17, 1999  
INVENTOR(S)  : Michael D. Delmore, Scott A. Burton, Nicholas R. Baumann, and Wayne K. Dunshee It is certified that error appears in the above-identified patent and that said Letters Patent is hereby corrected as shown below:

<u>Title page,</u>  
Item [75], after Nicholas R. Baumann, St. Paul., please insert therefor -- Wayne K. Dunshee, Maplewood --.

Signed and Sealed this

Twenty-seventh Day of November, 2001

*Attest:*

NICHOLAS P. GODICI  
*Attesting Officer*     *Acting Director of the United States Patent and Trademark Office*